United States Patent [19]

Domb

[11] Patent Number: 5,221,535
[45] Date of Patent: * Jun. 22, 1993

[54] SUSTAINED RELEASE FORMULATIONS OF INSECT REPELLENT

[75] Inventor: Abraham J. Domb, Baltimore, Md.

[73] Assignee: Nova Pharmaceutical Corporation, Baltimore, Md.

[*] Notice: The portion of the term of this patent subsequent to Feb. 23, 2010 has been disclaimed.

[21] Appl. No.: 826,215

[22] Filed: Jan. 23, 1992

Related U.S. Application Data

[63] Continuation of Ser. No. 607,542, Nov. 8, 1990, abandoned, which is a continuation-in-part of Ser. No. 435,546, Nov. 13, 1989, abandoned.

[51] Int. Cl.$^5$ ...................... A61K 31/47; A01N 25/00
[52] U.S. Cl. .................... 424/450; 424/405; 424/417; 424/403; 264/4.6; 428/402.2
[58] Field of Search ............... 424/450, 403, 405, 417; 428/402.2; 264/4.1–4.6

[56] References Cited

U.S. PATENT DOCUMENTS

| | | | |
|---|---|---|---|
| 3,004,892 | 10/1981 | Hainsworth et al. | 167/66 |
| 3,159,545 | 12/1964 | Kidwell et al. | 167/83 |
| 3,159,600 | 12/1964 | Watkins | 260/46.5 |
| 3,804,776 | 4/1974 | Yazawa et al. | 252/316 |
| 3,957,971 | 5/1976 | Oleniacz | 424/70 |
| 3,993,754 | 11/1976 | Rahman et al. | 424/177 |
| 4,010,038 | 3/1977 | Iwasaki et al. | 106/22 |
| 4,025,455 | 5/1977 | Shackle | 252/316 |
| 4,029,762 | 6/1977 | Galanos et al. | 424/87 |
| 4,089,801 | 5/1978 | Schneider | 252/316 |

(List continued on next page.)

FOREIGN PATENT DOCUMENTS

| | | |
|---|---|---|
| 0042249 | 12/1981 | European Pat. Off. . |
| 0167825 | 1/1986 | European Pat. Off. . |
| 0177368 | 4/1986 | European Pat. Off. . |
| 0270460 | 6/1986 | European Pat. Off. . |
| 0209870 | 1/1987 | European Pat. Off. . |
| 0274431 | 7/1988 | European Pat. Off. . |
| 2601207A | 7/1976 | Fed. Rep. of Germany . |
| WO 83/00294 | 3/1983 | PCT Int'l Appl. . |
| WO A 8500011 | 3/1985 | PCT Int'l Appl. . |
| 2135647A | 9/1984 | United Kingdom . |

OTHER PUBLICATIONS

Friedman, et al., *Drug Development and Industrial Pharmacy* 13 (9–11), 2067–2085 (1987).
Gasco, et al., *Il Farmaco-Ed. Pr.* 43(10) 326 (1987).
Gasco, et al., *International Journal of Cosmetic Science* 10(6), 263–269 (1988).
Kawamata, et al., *J. Pharm. Sci.* 76(11), S275, Abstract No. 04-W-19 (1987).
Schmidt, et al., *Acta Pharmaceutical Technologica* 38(1), 34 (1989).
Wang, et al., *J. Pharm. Sci. 76(11), S305, Abstract No. N 07-W-21 (1987).*
Wang, et al., *J. Pharm. Sci.* 76(11), S305, Abstract No. N 07-W-22.
Sasaki, et al., *J. Pharm. Dyn.* 7, 120–130 (1984).
Venkatesh, et al., *J. Pharm. Sci.* 76(11), S305, Abstract No. N 07-W-19.
Gao and Huang, *Biochim. Biophys. Acta* 897, 377–383 (1987).

*Primary Examiner*—Thurman K. Page
*Assistant Examiner*—G. S. Kishore
*Attorney, Agent, or Firm*—Kilpatrick & Cody

[57] ABSTRACT

A microsuspension system containing insect repellent is disclosed that includes liposheres, that are solid, water-insoluble microparticles that have a layer of a phospholipid embedded on their surface. The core of the liposphere is a solid insect repellent, or an insect repellent dispersed in an solid vehicle, such as a wax. Insect repellents include compounds that repel insects, are insecticidal, or regulate or inhibit insect growth on humans and other animals and plants. Insect repellent liposheres provide controlled release of insect repellents while minimizing absorption through the skin.

23 Claims, No Drawings

U.S. PATENT DOCUMENTS

| | | | |
|---|---|---|---|
| 4,145,410 | 3/1979 | Sears | 424/19 |
| 4,168,308 | 9/1979 | Wretlind et al. | 424/244 |
| 4,186,183 | 1/1980 | Steck et al. | 424/38 |
| 4,201,767 | 5/1980 | Fullerton et al. | 424/89 |
| 4,224,179 | 9/1980 | Schneider | 252/316 |
| 4,235,871 | 11/1980 | Papahadjopoulos et al. | 424/19 |
| 4,280,996 | 7/1981 | Okamoto et al. | 424/199 |
| 4,298,594 | 11/1981 | Sears et al. | 424/19 |
| 4,310,506 | 1/1982 | Baldeschwieler et al. | 424/1 |
| 4,317,743 | 3/1982 | Chang | 252/316 |
| 4,322,796 | 6/1982 | Los | 424/229 |
| 4,331,654 | 5/1982 | Morris | 424/38 |
| 4,349,529 | 9/1982 | Morcos et al. | 424/1 |
| 4,356,167 | 10/1982 | Kelly | 424/38 |
| 4,377,567 | 3/1983 | Geho | 424/1 |
| 4,404,183 | 9/1983 | Kawata et al. | 424/19 |
| 4,434,153 | 2/1984 | Urquhart et al. | 424/22 |
| 4,438,052 | 3/1984 | Weder et al. | 264/4.6 |
| 4,439,194 | 3/1984 | Harwood et al. | 604/890 |
| 4,446,165 | 5/1984 | Roberts | 426/602 |
| 4,448,765 | 5/1984 | Ash et al. | 424/14 |
| 4,460,560 | 7/1984 | Tokes et al. | 424/1.1 |
| 4,485,054 | 11/1984 | Mezei et al. | 264/4.6 |
| 4,492,720 | 1/1985 | Mosier | 427/213.3 |
| 4,515,736 | 5/1985 | Deamer | 264/4.3 |
| 4,544,545 | 10/1985 | Ryan et al. | 424/1.1 |
| 4,563,354 | 1/1986 | Chang et al. | 424/195.1 |
| 4,610,868 | 9/1986 | Fountain et al. | 428/402.2 |
| 4,725,442 | 2/1988 | Haynes | 424/490 |
| 4,752,485 | 6/1988 | Sharma et al. | 426/99 |
| 4,761,288 | 8/1988 | Mezel | 424/450 |
| 4,794,000 | 12/1988 | Ecanow | 424/457 |
| 4,797,288 | 1/1989 | Sharma et al. | 424/476 |
| 4,804,548 | 2/1989 | Sharma et al. | 426/96 |
| 4,816,247 | 3/1989 | Desai et al. | 424/80 |
| 4,828,857 | 5/1989 | Sharma et al. | 426/285 |
| 4,855,090 | 8/1989 | Wallach | 424/450 |
| 4,880,634 | 11/1989 | Speiser | 424/450 |
| 4,894,233 | 1/1990 | Sharma et al. | 424/440 |
| 4,894,234 | 1/1990 | Sharma et al. | 424/440 |
| 4,914,084 | 4/1990 | Ecanow | 514/6 |
| 4,929,508 | 5/1990 | Sharma et al. | 424/439 |
| 4,933,183 | 6/1990 | Sharma et al. | 424/439 |
| 4,935,242 | 6/1990 | Sharma et al. | 424/439 |
| 4,963,363 | 10/1990 | Forssen | 424/450 |
| 4,963,367 | 10/1990 | Ecanow | 424/485 |
| 4,973,465 | 11/1990 | Baurain et al. | 424/406 |

SUSTAINED RELEASE FORMULATIONS OF INSECT REPELLENT

This is a continuation of U.S. Ser. No. 07/607,542 which is abandoned which in turn is a continuation-in-part of U.S. Ser. No. 07/435,546, entitled "Lipospheres for Controlled Delivery of Substances," filed on Nov. 13, 1989, by Abraham J. Domb, now abandoned.

BACKGROUND OF THE INVENTION

This invention is in the area of controlling delivery devices for the administration of insect repellents.

Insects such as mosquitos, flies and fleas are a significant factor in the spread of many serious diseases of man and other animals. Examples include malaria, encephalitis, and a variety of parasites. They are also a general nuisance to humans and other animals. Efforts to repel these insect pests, other than with physical means, are generally ineffective for more than a few hours. There is also a significant economic loss associated with animals spending their efforts repelling insect rather than foraging.

Most means for repelling insects consist of applying an organic compound such as N,N-diethyl-m-toluamide (DEET) to the skin in an organic solvent. DEET is the most effective compound known to repel mosquitos, however, even its effectiveness is limited to a few hours. Moreover, the solvent in which it is applied to the skin also facilitates passage of the DEET through the skin, leading to undesirable toxicity, as well as irritation of the skin and eyes.

A variety of other compounds have been used to repel or kill other insects, especially flies and fleas. Most flea repellents or insecticides consist of a combination of active ingredients, many of which are not stable over a prolonged period of time. Efforts to extend the period of the effectiveness have not met with great success, although some microencapsulated forms are being marketed. These consist either of polymer or protein microcapsules incorporating the active agent to be released. The disadvantages of these reagents are that they are expensive to manufacture, they contain polymer residuals, and they are gritty and uncomfortable when applied to the skin.

It is therefore an object of the present invention to provide a composition and method to release insect repellents over an extended period of time, especially on the skin of a human or other animal.

It is a further object of the present invention to provide a composition and method to release insect repellents with minimum absorption through the skin or release of irritating chemicals at the application site.

It is another object of the present invention to provide a composition, and method of use thereof, for release of insect repellents, that is easy to prepare and stable for an extended period of time prior to use and in vivo.

SUMMARY OF THE INVENTION

Solid, water-insoluble lipospheres including a solid hydrophobic core formed of an insect repellent, alone or in combination with a carrier, having a layer of a phospholipid embedded on the surface of the core, are disclosed for use in providing extended release of active agent.

Lipospheres can be prepared by: (1) forming a liquid solution or suspension of the insect repellent by either melting the repellent, or dissolving or dispersing the repellent in a liquid vehicle to form a liquid repellent that solidified at room temperature or greater; (2) adding phospholipid and an aqueous solution to the liquid repellent to form a suspension; (3) mixing the suspension at a temperature above the melting temperature until a homogeneous fine dispersion is obtained; and then (4) rapidly cooling the dispersion to below the melting temperature of the liquid mixture containing the repellent. The liposheres formed by this process have a diameter of greater than one micron coated with a layer of a phospholipid. The hydrophobic side of the phospholipid is embedded in the surface of the solid hydrophobic core and the hydrophilic side of the phospholipid interfaces with the aqueous solution.

Lipospheres can be designed to release repellent over a period of several hours to approximately four or five days, or longer, by varying the ratio of carrier to repellent in the core, by choice of carrier, concentration of formulation and amount of liposphere administered. For application of an insect repellent such as DEET to human skin, it is preferred to have release for between several hours and one day.

Examples demonstrate the sustained release of DEET over a period of days when applied topically to human skin, as measured by its effectiveness in repelling mosquitos.

DETAILED DESCRIPTION OF THE INVENTION

A delivery system for insecticides and insect repellents is described that results in an extended period of release of active agent. As used herein, "insect repellent" refers to compounds killing, repelling or preventing an increase in insect growth or populations. The delivery system are the liposphaeres described in copending U.S. Ser. No. 07/435,546 entitled "Liposphaeres for Controlling Delivery of Substances," filed on Nov. 13, 1989, by Abraham J. Domb.

The liposphaeres are distinct from microdroplets, vesicles or liposomes since the liposphaeres have solid inner cores at room temperature. The liposphaeres are distinct from microspheres of uniformly dispersed material in homogenous polymer since they consist of at least two layers, the inner solid particle and the outer layer of phospholipid.

The combination of solid inner core with phospholipid exterior confers several advantages on the liposphaeres as compared with conventional microspheres and microparticles, including high dispersibility in an aqueous medium, and a release rate for the entrapped substance that is controlled by the phospholipid coating and the carrier. There are also many advantages over the other dispersion based delivery systems. Liposphaeres have increased stability as compared to emulsion based delivery systems, including vesicles and liposomes, and are more effectively dispersed than most suspension based systems. Further, the substance to be delivered does not have to be soluble in the vehicle since it can be dispersed in the solid carrier. Liposphaeres also have a lower risk of reaction of substance to be delivered with the vehicle than in emulsion systems because the vehicle is a solid inert material. Moreover, the release rate of the substance from the liposphaeres can be manipulated by altering either or both the inner solid vehicle or the outer phospholipid layer. Liposphaeres are also easier to prepare than vehicles such as liposphaeres, and are inherently more stable. Stability has become the major problem limiting the use of liposomes, both in terms of shelf life and after administration to a patient. Liposomes and vesicles do not remain intact or available in vivo after injection for more than a few hours to a couple of days. Unlike many of the biodegradable polymeric systems, the liposphere not made with biodegradable polymers are stable in aqueous solutions. As importantly, the cost of the reagents for making the liposphere (food grade) is significantly less than the cost of reagents for making liposomes, which require very pure lipids. For example, food grade lecithin costs about $2 per pound (from Central Soya Co., Ft. Wayne, Ind.), as compared with liposome grade lecithin which costs about $500 per pound (Avanti Polar Lipids Inc., Pelham, Ala.).

The lipospheres containing the insect repellents are administered to the environment or the skin of a human or other animal or repel or kill insects. The lipospheres are preferably administered to the environment by spraying an aqueous dispersion of the lipospheres in the area where insect control is desired. The lipospheres are preferably administered to a human or other animal by spraying an aqueous dispersion of lipospheres or by topically applying the lipospheres in an aqueous solution, ointment, cream, or other appropriate carrier. The liposphere formulations are stored in aqueous buffer, freeze dried, or in a ointment or cream base, in the freezer, refrigerator or room temperature, and are stable for an extending period of time.

PREPARATION OF THE LIPOSPHERES

The preparation and modification of lipospheres is described first with reference to the following general descriptions and then with reference to the following non-limiting examples of the preparation and application of lipospheres.

Selection of the Solid Core of the Liposphere.

In the preferred embodiment, the liposphere contains a core that has a melting temperature equal to or greater than room temperature, approximately 25° C. For example, for preparation of lipospheres to be applied to the skin, the core is prepared by choosing an insect repellent that has a melting temperature of approximately 30° C., or by mixing the insect repellent in a carrier to produce a mixture having a melting point of approximately 30° C. The repellent, or repellent and carrier, preferably has a melting point of less than 120° C. and is stable in the liquid form when mixed with hot aqueous media.

The carrier must be compatible with the insect repellent. Suitable solid carriers are inert hydrophobic biocompatible materials with a melting range between 30° and 120° C. Examples are natural, regenerated, or synthetic waxes such as beeswax and carnauba wax; cholesterol; fatty acid esters such as ethyl stearate, isopropyl myristate, and isopropyl palmitate; high molecular weight fatty alcohols such as cetostearyl alcohol, cetyl alcohol, stearyl alcohol, and oleyl alcohol; solid hydrogenated castor and vegetable oils; hard and soft paraffins; hard fat such as tristearin; biodegradable polymers such as polycaprolactone, polyamides, polyanhydrides, polycarbonates, polyorthoesters, polyactic acids, and copolymers of lactic acid and glycolic acid; cellulose derivatives and mixtures thereof. These and other suitable materials are known to those skilled in the art and most are commercially available, as demonstrated by the extensive list of suitable carrier materials in Martindale, *The Extra Pharmacopoeia,* The Pharmaceutical Press, 28th Edition pp 1063–1072 (1982).

The release rate of the repellent from the liposphere is dependent in part upon the composition of the core, as well as the outer phospholipid layer, and can be altered by varying the compositions appropriately.

It is often desirable to deliver a water soluble repellent to a targeted area, or to control the release of a water soluble substance. Since the inner core of the liposphere is hydrophobic, it is necessary to decrease the water solubility of the repellent before liposphere preparation. Methods to decrease water solubility include using a water insoluble salt or base, complex, or insoluble precursor form of the repellent; preincorporating the repellent into hydrophobic microparticles that can be used as repellent particles; or preparing an aqueous medium that the repellent is less soluble in, for example, by adjustment of pH or ionic strength, or by adding salts or additives. If the repellent is rendered less water soluble by adjustment of pH or ionic strength, the resulting lipospheres can be isolated by filtration or centrifugation and reconstituted with an appropriate buffer solution prior to use.

Active materials can be preincorporated into microparticles of a hydrophobic solid phase, such as tristearin (melting point 65° C. to 72° C.), that can then be incorporated into lipospheres with a vehicle having a lower melting point, such as ethyl stearate (melting point 35° C.), to avoid melting the tristearin particles containing the active material. In this form, the tristearin-active material particles are the hydrophobic "repellent" which is dispersed in the ethyl stearate liposphere. The formulations can then be freeze dried with standard techniques and reconstituted prior to use. Selection of the Phospholipic Coating.

The solid core of the liposphere is coated with one or more phospholipids that are embedded into the surface of the solid core during manufacture. Mixtures of two or more phospholipids can be used to vary the surface properties and reactivity of the liposphere. In some embodiments the phospholipid may be selected to enhance adhesion of the lipospheres to the surfaces to which they are applied.

Pholpholipid

A phospholipid is a phosphorylated diacylglyceride molecule or its derivative. The parent structure is diacylglycerol phosphate, or phosphatidic acid. Phosphatidyl choline (lecithin) is the choline ester of phosphorylated diacylglyceride. Synthetic lecithin are available with acyl chain lengths ranging from 4 to 19 carbons. The preferred lecithins for biological applications are those with alkyl chain lengths in the biological range (10 to 18 carbons). Naturally occurring lecithin can be obtained from a variety of sources such as egg, bovine heart, or soy bean. Unsaturated lecithins (dioleoyl; dilinoleoyl; alpha-palmitoyl, beta oleoyl; alpha palmitoyl, beta linoleoyl; and alpha oleoyl, beta palmitoyl), dianachidonyl lecithin (highly unsaturated and a prostaglandin precursor), and alpha palmito beta myristoyl lecithin are also available.

A molecule somewhat structurally related to phosphatidic acid, sphingomyelin, is also suitable for use in the coating of lipospheres.

Certain phospholipids, such as phosphatidic acid, phosphatidyl serine, phosphatidyl inositol, cardiolipin (diphosphatidyl glycerol), and phosphatidyl glycerol, can react with calcium, causing aggregation or the binding of lipospheres to cell membranes. These reactions can be minimized by combining these phospholipids with non-calcium binding phospholipids such as phosphatidyl choline. Phosphatidic acid can be isolated from egg or prepared synthetically (dimyristolyl, dipalmitoyl and distearoyl derivatives are available from Calbiochem). Bovine phosphatidyl serine is also available commercially (Sigma Chemical Co., St. Louis, Mo.). Phosphatidyl inositol can be isolated from plant or bovine sources. Cardiolipin can be purified from bovine or bacterial sources. Phosphatidyl glycerol can also be purified from bacterial sources or prepared synthetically.

Phosphatidyl ethanolamine in the pure state self-aggregates in a calcium-independent fashion, and is believed to have strong tendencies to aggregate with cell membranes. It should therefore be used in combination with non-aggregating phospholipids. Phosphatidyl ethanolamine is commercially available, isolated from egg, bacteria, bovine, or plasmalogen or as the synthetic dioctadecanoyl, dioleoyl, dihexadecyl, dilauryl, dimyristolyl and dipalmitoyl derivatives.

For cost efficiency, non-injectable food grade lecithins can be used to formulate the liposheres, such as Centrolex TM or Actiflo TM 70SB, which are lecithins extracted from soya beans manufactured by Central Soya, Ft. Wayne, Ind.

Steroids

Steroids such as cholesterol (a natural constituent of membranes), estrogens, (such as estriol, estrone, estradiol and diethylstilbestrol), and androgens (such as androstenedione and testosterone) cannot function alone as the liposhere coating but may be incorporated into the phospholipic surface coating, as well as serve as the core material.

Amphiphiles

Amphiphiles can be added to the phospholipic coating to alter the surface charge on the liposhere. Examples of amphiphiles that produce a positive charge on the coating are protonated along chain alkyl amines such as stearylamine or the corresponding secondary, tertiary or quaternary substituted amines. Examples of amphiphiles that produce a negative charge are arachidonic acid and other fatty acids.

Surfactants

The phospholipids can be substituted in part with surfactants such as Tween TM (a hydrophilic class of surfactants), Span TM (a hydrophobic class of surfactants), and polyethylene glycol surfactants. Selection of Repellent.

A number of biologically active agents for control of insects are known and commercially available which are suitable for delivery in liposheres. The types of insects that can be targeted for control include flying insects such as mosquitos, flies, wasps, yellow jackets, hornets and bees, ants, roaches, lice, fleas, and scabies, as well as many insects that eat or lay their eggs or plants.

A preferred compound for repelling mosquitos and flies is DEET (N,N-diethyl-m-toluamide). A preferred compound for inhibiting insect maturation and reproduction is the insect growth regulator (S)-methoprene [isopropyl (2E,4E,7S)-11-methoxy-3,7,11-trimethyl-2,4-dodecadienoate], marketed as Precor TM by Sandox Ltd. Preferred compounds for killing fleas are pyrethrins, piperonyl butoxide, N-octyl bicycloheptene dicarboximide, and 2,3:4,5-Bis (2-butylene) tetrahydro-2-furaldehyde. Other compounds that are marketed for insect control include dimethyl phthalate (DMP), 1,3-ethyl hexanediol (EHD), 1-(3-cyclohexan-1-ylcarbonyl)-2-methylpiperidine (CYM), 1-(3-cyclohexan-1-ylcarbonyl)-2-piperdine (CYP), and phosphorothioic acid O,O-diethyl O-[6-methyl-2-(I-methylethyl)-4-pyrimidinyl]ester, marketed as Diazinon TM by Ortho.

Representative agents to repel insects from plants include plants oils (neem, citronella, eucalyptus, marcosa, turpentine); amines (2-(2-methylamino-ethyl)-pyridine, 3-(methylaminomethyl)-pyridine, cadaverine, 1,8-diaminooctane, spermine, polyethyl eneimine); pesticides (cypermethrin, permethrin, carbofuran, chlormequat, carbendazim, benomyl, fentinhydroxide); carboxylic acids (n-decanoic and dodecanoic), and natural products such as polydogial and azadirctin.

These insect repellents/insecticides/insect growth regulators can be combined with other agents for control of pests, such as rodenticides, or with agents that attract insects, such as pheremones or flavorings, to increase the effectiveness of insecticides or growth regulators. They can be formulated for topical application, for application by spraying, or by application as an aerosol.

These compounds can be combined with other agents such as fertilizers, herbicides (such as atrazine, 1-chloro-4-ethylamino-6-isopropylamino-s-triazine) and fungicides for use in treating or killing plants, topically or systemically. They can also be combined with agents that provide a pleasant smell (such as benzyl acetate, citronellol, rhodinol, phenylethyl alcohol, and bergamet oil) or prevent odor or drying of the skin and hair (such as antiperspirants and deodorants and lotions), for topical application to the skin.

The effective concentration is determined empirically by comparing effectiveness of formulations containing different quantities of active agents. A preferred concentration of lipospheres containing DEET is between 1 and 50% by weight. Melt preparation of Lipospheres.

In the preferred embodiment, lipospheres are prepared by: (1) melting the repellent, or dissolving or dispersing the repellent in a liquid vehicle to form a liquid repellent which can be solidified by decreasing temperature; (2) adding phospholipid along with an aqueous medium to the liquid repellent at a temperature higher than the melting temperature of the liquid repellent to form a suspension of the repellent; (3) mixing the suspension at a temperature above the melting temperature of the liquid repellent until a homogeneous fine preparation is obtained; and then (4) rapidly cooling the preparation to below the melting temperature to solidify the liquid core.

Suitable methods of mixing the suspension include mechanical shaking or stirring, fine mixing using homogenizing and sonication.

Solvent Preparation of Lipospheres.

Alternatively, lipospheres can be prepared by solvent processing. This method of preparation of lipospheres involves the use of a solvents. The repellent, carrier, and phospholipid are dissolved or mixed in an organic solvent. The solvent is then evaporated, and the resulting solid is mixed with an appropriate amount of buffer and mixing continued until a homogeneous mixture is obtained. The temperature is then reduced to 10° C. with continuation mixing for approximately five minutes to form a milky suspension of lipospheres.

In an aqueous solution, the lipospheres form a uniform fine dispersion of microspheres coated with a layer of a phospholipid, with the hydrophobic side of the phospholipid embedded in the outermost layer of the solid hydrophobic core and the hydrophilic side at the aqueous interface. The particle size, particle distribution, and phospholipid coating can be altered by varying the concentration and properties of the solid vehicle, the lipid, and the mixing method.

The method of preparation of lipospheres, and resulting lipospheres containing repellent, described herein is simple and is characterized by high loading, reproducibility, versatility, and stability. The method and compositions are further illustrated by the following non-limiting examples.

Lipospheres encapsulating DEET were prepared. The liposphere formulations are superior to the formulations now being marketed in several respects. For example, the marketed preparations provide relief for only few hours. Moreover, the concentration of DEET is those formulations is extremely high, about 75 percent. This is particularly harmful because DEET is partially absorbed through skin. There have been several reports of adverse systemic effects associated with the use of DEET. The formulations described herein provide extended relief using low percent incorporation of DEET.

EXAMPLE 1

Preparation of Tristearin liposphere sustained release formulations of DEET.

500 mg of DEET was mixed with 1.0 gm of tristearin in a scintillation vial. The scintillation vial precoated with 500 mg of phosphatidyl choline (PCS). The scintillation vial was heated to 60° C. to obtain a uniform solution of DEET and tristearin. 10 ml of 0.1M phosphate buffer, pH 7.4 was added to the vial and the contents were mixed by vortexing. After obtaining a uniform dispersion, mixing was continued with intermitted cooling in a dry ice/acetone bath. The resulting formulation was a uniform, smooth textured paste.

Other formulations were prepared by varying the ratio of DEET, tristearin and PCS, as shown in Table 1.

EXAMPLE 2

Preparation of Polycaprolactone liposphere sustained release formulations of DEET.

500 mg of DEET was mixed with 1.0 gm of polycaprolactone in a scintillation vial. The scintillation vial was precoated with 500 mg of phosphatidyl choline (PCS). the scintillation vial was heated to 60° C. to obtain a uniform solution of DEET and polycaprolactone. 10 ml of 0.1M phosphate buffer, pH 7.4 was added to the vial and the contents were mixed using vortex. After obtaining a uniform dispersion, mixing was continued with intermitted cooling in a dry ice/acetone bath. The resulting formulation was a smooth, uniform textured paste.

EXAMPLE 3

Preparation of DEET lipospheres using the solvent method.

To a round bottom flask containing 100 grams of glass beads (3 mm in diameter), 50 ml of chloroform was added. 1 gm of PCS, 1 gm of tristearin and 0.5 g of DEET was added to the flask and mixed thoroughly till a clear solution was obtained. The chloroform was evaporated using a rotoevaporator under reduced temperature at room temperature. The temperature was raised to 40° C. after 20 minutes, to ensure complete removal of chloroform. A thin film of solids was obtained around the bottom flask and the glass beads. Ten milliliter of 0.9 % saline was added to the round bottom flask and the contents were mixed for 5 to 10 minutes at room temperature. The temperature was then lowered to 10° C. by placing the flask in crushed ice and mixing was continued for another half hour.

The resulting lipospheres were spherical in shape, with an average particle size of between 8 and 15 microns.

EXAMPLE 4

Preparation and comparison of appearance of DEET lipospheres having different liposphere formulations.

DEET formulations were prepared using the various compositions at a ratio of 1:2:1 DEET, carried, and phosphatidyl choline, up to 10% in water. The carriers used were: tripalmitin, beeswax, stearic acid, ethylstearate, and stearyl alcohol. The phosphatidyl cholines used were: lecithin from egg yolk and from soybean, and partially hydrogenated phosphatidyl choline.

All formulations were milky in appearance with an average particle size of 10 to 30 microns.

EXAMPLE 5

Preparation of CCP repellent lipospheres.

Lipospheres containing 10% 1-(3-cyclohexen-1-ylcarbonyl)piperidine (CCP) were prepared by the method described in Example 1 or by the method described in Example 3. The lipospheres were either CCP:Tristearin: PCE 1:2:1 or 1:1:1, by weight.

EXAMPLE 6

Demonstration of In vivo efficacy of tristearin and polycaprolactone DEET lipospheres.

Efficacy Test:

In vivo efficacy tests were conducted on human volunteers who had given informed consent. The formulations prepared in examples 1 and 2 were applied to forearms at various doses, and subjects exposed to mosquitos at various time intervals. The experimental environment consisted of a cylindrical chamber of fixed dimensions, equipped with 16×18 mesh mosquito netting. The device contained between ten and twelve fasted mosquitoes having access to the skin through the mosquito netting. The forearm was placed on the mosquito netting and the behavior of the insects was observed. The time over which no mosquitos landed on the skin (100% repellency) was the index for determining the effectiveness of the formulation.

The results of the studies on the tristearin and polycaprolactone DEET lipospheres are summarized in Table 1.

TABLE 1

Effectiveness of DEET lipospheres[a] in repelling insects.

| DEET % (w/w) | Core material % (w/w) | PCS % (w/w) | DEET applied mg/cm$^2$ | Area | Effectiveness (hrs) |
|---|---|---|---|---|---|
| | Tristearin | | | | |
| 5 | 20 | 10 | 0.125 | 4 | 2 |
| 5 | 10 | 5 | 0.125 | 4 | 3.0 |
| 5 | 20 | 10 | 0.125 | 4 | 2.5 |
| 5 | 10* | 5 | 0.125 | 4 | 3.5 |
| 0 | 20 | 10 | 0 | 4 | 0 |
| 10 | 10 | 10 | 0.25 | 4 | 3 |
| 10 | 30 | 10 | 0.25 | 4 | 4 |
| 15 | 30 | 10 | 0.50 | 4 | 4 |

TABLE 1-continued

Effectiveness of DEET liposphere[a] in repelling insects.

| DEET % (w/w) | Core material % (w/w) | PCS % (w/w) | DEET applied mg/cm² | Area | Effectiveness (hrs) |
|---|---|---|---|---|---|
| | Polycaprolactone | | | | |
| 5 | 10 | 5 | 0.50 | 19.63 | 2.5 |
| 5 | 20 | 10 | 0.50 | 19.63 | 2.2 |
| 5 | 10* | 5 | | | |
| 0 | 20 | 10 | 0 | 19.63 | 0 |
| 15 | 30 | 10 | 0.75 | 19.63 | 5 |

[a] 2.5 mg/cm² of each formulation applied.

EXAMPLE 7

Preparation and efficacy of tristearin-PCE liposheres containing different DEET concentrations.

Eight formulations containing 5 and 10% W/W DEET (4 of each concentration) were prepared and tested for repellency activity. All formulations contain tristearin as vehicle, egg yolk lecithin (PCE), DEET and phosphate buffer solution pH 7.4 added to 10 ml. The formulations were prepared as described in Example 1 and tested as described in Example 6 and 8. Table 2 summarizes the formulation compositions and efficacy as determined according to example 6.

TABLE 2

Comparison of repellency of liposheres containing either 5% or 10% DEET.

| | Composition[a] (grams) | | | Period of Repellency (hours) |
|---|---|---|---|---|
| | DEET | Tristearin | PCE | |
| A | 1.0[b] | 1.5 | 0.5 | 5 |
| B | 1.0[b] | 1 | 1 | 5 |
| C | 1.0[b] | 2 | 0.5 | >6 |
| D | 1.0[b] | 3 | 1 | 4 to 5 |
| E | 0.5 | 0.75 | 0.25 | 2 to 3 |
| F | 0.5 | 0.5 | 0.5 | 2 to 3 |
| G | 0.5 | 1 | 0.25 | 2 to 3 |
| H | 0.5 | 1.5 | 0.5 | 2 to 3 |

[a] One gram DEET is equal to 10.0% DEET.
[b] Testing and results described in examples 7 and 8.

EXAMPLE 8

Comparison of the effectiveness of DEET liposheres in repelling two different species of mosquitos.

Method for testing repellency.

The repellent was applied to four locations on each arm. One ounce cups with screen bottoms containing five avid (displaying host-seeking behavior) mosquitoes, with Aedes aegypti or Anopheles stephensi, were placed on the treated portions of skin. Mosquitoes were also placed on an untreated section of the arm to serve as a control. After a ten minute period the cups were removed and the number of biting mosquitoes (evident by a blood meal) were counted. This procedure was repeated with previously unexposed mosquitoes every fifteen minutes in the first half hour (with Aedes aegypti only) after application and on every half hour thereafter for a total of four hours after application. Both mosquito species tested: Aedes aegypti and Anopheles stephensi are extremely aggressive biters in this test.

The formulations A, B, C, and D, described in Table 2, were applied at 2.5 mg per cm² of skin surface. Formulations A (1.0 g DEET, 1.5 g tristearin, 0.5 g PCE to 10 ml with buffer) and C(1.0 g DEET, 2 g tristearin, 0.5 g PCE to 10 ml with buffer) were uniform in consistency and applied easily, whereas B (1.0 g DEET, 1 g tristearin, 1 g PCE to 10 ml with buffer) and D (1.0 g DEET, 3 g tristearin, 1 g PCE to 10 ml with buffer) were more paste-like and proved difficult to spread.

TABLE 3

Comparison of effectiveness of DEET liposheres against two species of mosquitos.

| Time after application (min) | Total number biting | | | | |
|---|---|---|---|---|---|
| | Aedes aegypti (Anopheles stephensi) | | | | |
| | Formulations | | | | |
| | A | B | C | D | Control |
| 15 min | 0 | 0 | 0 | 0 | 4 |
| 30 | 0 (0) | 0 (0) | 0 (0) | 0 (0) | 5 (0) |
| 60 | 0 (0) | 0 (0) | 0 (0) | 0 (1) | 5 (3) |
| 90 | 0 (0) | 0 (0) | 0 (0) | 0 (1) | 5 (2) |
| 120 | 0 (0) | 0 (0) | 0 (0) | 0 (0) | 5 (3) |
| 150 | 0 (1) | 0 (0) | 0 (0) | 0 (0) | 5 (5) |
| 180 | 0 (1) | 0 (0) | 0 (0) | 0 (0) | 4 (4) |
| 210 | 0 (1) | 1 (1) | 0 (0) | 0 (1) | 4 (2) |
| 240 | 0 (2) | 0 (1) | 0 (2) | 0 (0) | 0 (2) |
| 270 | 0 (2) | 0 (2) | 0 (2) | 0 (1) | 1 (5) |

Tested against Aedes Aegypti the formulations proved to be repellent, based on prevention of biting, for a minimum of 3.5 hours. At this point there was breakthrough biting on formulation B. Beyond this point in time no further biting occurred on treated surfaces, although biting on the untreated surface dropped as well, presumably because this occurred at a time host-seeking behavior often ceases for Aedes aegypti.

Findings for Anopheles stephensi are not as clear cut. Biting on the untreated surface is more erratic and there was early breakthrough biting on some formulations, notably formulation D. By four hours there was breakthrough biting on all formulations. The literature on mosquito repellency has repeatedly reported limited repellency for DEET tested against Anopheline mosquitoes.

In conclusion, these formulations are repellent to Aedes aegypti for a minimum of four to six hours. It is likely that some of these formulations are effective beyond this point. The fact that formulation C was effective against Anopheles stephensi for four hours, combined with the A. aegypti findings suggest that C is the most promising repellent tested at this time.

Modifications and variations of the present invention, liposphere delivery systems for insect repellents, insect controls, and insecticides, will be obvious to those skilled in the art from the foregoing detailed description. Such modifications and variations are intended to come within the scope of the appended claims.

I claim:

1. A liposphere comprising:
   a core formed of a hydrophobic material existing as a solid at a temperature of 25° C. and having insect repellent or insecticidal activity, and
   a phospholipid coating surrounding the core,
   wherein the hydrophobic ends of the phospholipid are embedded in the solid core and the hydrophilic ends of the phospholipid arm exposed on the surface of the liposphere,
   the combination forming a spherical structure having an average particle diameter between 0.35 and 250 microns.

2. The liposphere of claim 1, wherein the repellent or retardant activity is produced by a compound incorporated into the hydrophobic core selected from the group consisting of insect repellents, insect growth regulators and insecticides.

3. The liposphere of claim 1, wherein the repellent compound is selected from the group consisting of N,N-diethyl-m-toluamide, (S)-methoprene, pyrethrins, piperonyl butoxide, N-octyl bicycloheptene dicarboximide, and 2,3:4,5-Bis (2-butylene) tetrahydro-2-furaldehyde, dimethyl phthalate, 1,3-ethyl hexanediol, 1-(3-cyclohexan-1-ylcarbonyl)-2-methylpiperidine, 1-(3-cyclohexan-1-ylcarbonyl)-2-piperidine, phosphorothioic acid O,O-diethyl O-[6-methyl-2-(I-methylethyl)-4-pyrimidinyl]-ester, [plants oils,] 2-(2-methylamino-ethyl)-pyridine, 3-(methylaminomethyl)-pyridine, cadaverine, 1,8-diaminooctane, spermine, polyethyl eneimine, cypermethrin, permethrin, carbofuran, chlormequat, carbendazim, benomyl, fentinhydroxide, n-decanoic and dodecanoic carboxylic acids, polydogial and azadirctin.

4. The liposphere of claim 2 in a composition further comprising a compound selected from the group consisting of plant fertilizers, fungicides, rodenticides, herbicides, skin care supplements, fragrances, antiperspirants and deodorants.

5. The liposphere of claim 4 wherein the solid core comprises the repellent in a vehicle for the repellent, which in combination with the repellent exists as a solid at 30° C.

6. The liposphere of claim 5 wherein the vehicle is selected from the group consisting of natural, regenerated and synthetic waxes, fatty acid esters, high molecular weight fatty alcohols, solid hydrogenated plant oils, solid triglyceride, and biodegradable natural and synthetic polymers.

7. The liposphere of claim 1 wherein the repellent is N,N-diethyl-m-toluamide in a concentration of between 1 and 50% by weight.

8. The liposphere of claim 1 in a carrier for topical administration to animals or to plants.

9. A method for killing or repelling insects comprising administering lipospheres formed of a core formed of a hydrophobic material existing as a solid at 25° C. having insect repellent or insecticidal activity, and a phospholipid coating surrounding the core, wherein the hydrophobic ends of the phospholipid are embedded in the solid core and the hydrophilic ends of the phospholipid are exposed on the surface of the liposphere, the combination forming a spherical structure having an average particle diameter between 0.35 and 250 microns.

10. The method of claim 9 wherein the repellent or insecticidal activity is produced by a compound incorporated into the hydrophobic core selected from the group consisting of insect repellents, insect growth regulators and insecticides.

11. The method of claim 9 wherein the repellent compound is selected from the group consisting of N,N-diethyl-m-toluamide, (S)-methoprene, pyrethrins, piperonyl butoxide, N-octyl bicycloheptene dicarboximide, and 2,3:4,5-Bis (2-butylene) tetrahydro-2-furaldehyde, phosphorothioic acid O,O-diethyl O-[6-methyl-2-(I-methylethyl)-4-pyrimidinyl]ester, [plants oils,] 2-(2-methyloamino-ethyl)-pyridine, 3-(methylaminomethyl)-pyridine, cadaverine, 1,8-diaminooctane, spermine, polyethyl eneimine, cypermethrin, permethrin, carbofuran, chlormequat, carbendazim, benomyl, fentinhydroxide, n-decanoic and dodecanoic carboxylic acids, polydogial and azadirctin.

12. The method of claim 9 further comprising adding the lipospheres to a mixture comprising a compound selected from the group consisting of plant fertilizers, fungicides, rodenticides, herbicides, skin care supplements, fragrances, antiperspirants and deodorants.

13. The method of claim 9 wherein the solid core includes the insect repellent and a vehicle for the repellent, which in combination with the repellent exists as a solid at 30° C.

14. The method of claim 13 wherein the vehicle is selected from the group consisting of natural, regenerated and synthetic waxes, fatty acid esters, high fatty alcohols, solid hydrogenated castor and vegetable oils, solid triglyceride, and biodegradable polymers.

15. The method of claim 9 for insect control further comprising preparing a dispersion of the lipospheres in an aqueous solution and spraying the dispersion onto animals or plants.

16. The method of claim 9 for insect control in an area further comprising dispersing the lipospheres throughout the area where insect populations are to be controlled.

17. The method of claim 9 for repelling insects further comprising dispersing the lipospheres in a carrier for topical application to animals or plants.

18. The method of claim 17 further comprising spreading the lipospheres on the skin of the animals to which the lipospheres are applied.

19. The method of claim 9 further comprising preparing lipospheres by forming a non-aqueous liquid of the hydrophobic core material.

adding phospholipid and an aqueous solution to the liquid core material, and mixing the liquid core material and phospholipid until a suspension of lipospheres is formed.

20. The method of claim 19 further comprising sonicating and cooling the liquid core material and phospholipid after mixing to form the solid core.

21. The method of claim 19 wherein the liquid core material and phospholipid are heated during mixing to a temperature equal to or greater than the melting temperature of the core material.

22. The method of claim 19 where the liquid core material includes an organic solvent, further comprising evaporating the solvent while mixing the core material and phospholipid.

23. The method of claim 22 further comprising adding an aqueous buffer to the evaporated core material-phospholipid mixture and mixing until a suspension of lipospheres is formed.

* * * * *